United States Patent
Imai

(10) Patent No.: US 9,757,011 B2
(45) Date of Patent: Sep. 12, 2017

(54) DISTAL END RIGID SECTION OF INSERTION PORTION OF ENDOSCOPE AND ENDOSCOPE

(71) Applicant: OLYMPUS CORPORATION, Tokyo (JP)

(72) Inventor: Shunichi Imai, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 477 days.

(21) Appl. No.: 14/287,960

(22) Filed: May 27, 2014

(65) Prior Publication Data

US 2014/0330081 A1 Nov. 6, 2014

Related U.S. Application Data

(63) Continuation of application No. PCT/JP2013/063821, filed on May 17, 2013.

(30) Foreign Application Priority Data

Jul. 19, 2012 (JP) ................... 2012-160506

(51) Int. Cl.
*A61B 1/00* (2006.01)
*A61B 1/06* (2006.01)
(Continued)

(52) U.S. Cl.
CPC ........ *A61B 1/00078* (2013.01); *A61B 1/0008* (2013.01); *A61B 1/0011* (2013.01);
(Continued)

(58) Field of Classification Search
CPC .............. A61B 1/0008; A61B 1/00096; A61B 1/00101; A61B 1/00163; A61B 1/0661;
(Continued)

(56) References Cited

U.S. PATENT DOCUMENTS 8,269,828 B2 * 9/2012 Miller ................ A61B 1/00052
348/80
9,060,677 B2 * 6/2015 Imai ................... A61B 1/00091
(Continued)

FOREIGN PATENT DOCUMENTS

JP A-8-286127 11/1996
JP A-2001-218728 8/2001
(Continued)

OTHER PUBLICATIONS

Office Action issued in Japanese Patent Application No. 2014-521388 mailed Jul. 8, 2014 (with translation).
(Continued)

*Primary Examiner* — John P Leubecker
*Assistant Examiner* — Rajaa El Alami
(74) *Attorney, Agent, or Firm* — Oliff PLC

(57) ABSTRACT

A distal-end rigid section of an insertion section of an endoscope, includes: a first base of a metallic material, which constitutes a distal-end portion of the insertion section of the endoscope; a second base of a resin material, which is formed on an axially proximal-end side of the first base; a cylindrical portion protruding from the second base toward an axially distal-end side of the first base and including a non-circular hole portion in which an illumination light source having a non-circular outer shape, generating light and emitting illumination light is disposed; and a through-hole formed by opening a part along an outer peripheral surface of the first base, the cylindrical portion being disposed in the through-hole such that the illumination light is emitted to the axially distal-end side of the first base.

12 Claims, 13 Drawing Sheets

(51) Int. Cl.
*G02B 23/24* (2006.01)
*A61B 1/015* (2006.01)
*A61B 1/018* (2006.01)
*A61B 1/05* (2006.01)

(52) U.S. Cl.
CPC ...... *A61B 1/00096* (2013.01); *A61B 1/00101* (2013.01); *A61B 1/00105* (2013.01); *A61B 1/00163* (2013.01); *A61B 1/015* (2013.01); *A61B 1/018* (2013.01); *A61B 1/05* (2013.01); *A61B 1/06* (2013.01); *A61B 1/0661* (2013.01); *A61B 1/0676* (2013.01); *A61B 1/0684* (2013.01); *G02B 23/2476* (2013.01)

(58) Field of Classification Search
CPC .. A61B 1/00105; A61B 1/0676; A61B 1/0684
See application file for complete search history.

(56) References Cited

U.S. PATENT DOCUMENTS

| | | | | |
|---|---|---|---|---|
| 9,532,707 | B2* | 1/2017 | Sugiyama | A61B 1/127 |
| 2001/0007051 | A1 | 7/2001 | Nakashima | |
| 2007/0173695 | A1* | 7/2007 | Hirata | A61B 1/00096 |
| | | | | 600/152 |
| 2011/0282148 | A1* | 11/2011 | Kase | A61B 1/00177 |
| | | | | 600/113 |
| 2012/0010465 | A1* | 1/2012 | Erikawa | A61B 1/05 |
| | | | | 600/109 |
| 2012/0232343 | A1* | 9/2012 | Levy | A61B 1/00177 |
| | | | | 600/109 |
| 2013/0131447 | A1* | 5/2013 | Benning | A61B 1/00137 |
| | | | | 600/109 |
| 2013/0137925 | A1* | 5/2013 | Ushijima | A61B 1/051 |
| | | | | 600/109 |
| 2014/0018613 | A1* | 1/2014 | Scott | A61B 1/00193 |
| | | | | 600/102 |
| 2014/0296638 | A1* | 10/2014 | Komukai | A61B 1/0653 |
| | | | | 600/121 |
| 2017/0108690 | A1* | 4/2017 | St. George | G02B 23/2469 |

FOREIGN PATENT DOCUMENTS

| | | |
|---|---|---|
| JP | A-2002-272672 | 9/2002 |
| JP | A-2005-270391 | 10/2005 |
| JP | A-2008-036033 | 2/2008 |
| JP | A-2010-091986 | 4/2010 |
| WO | WO 2006/001377 A1 | 1/2006 |

OTHER PUBLICATIONS

International Search Report issued in International Application No. PCT/JP2013/063821 mailed Aug. 20, 2013.

* cited by examiner

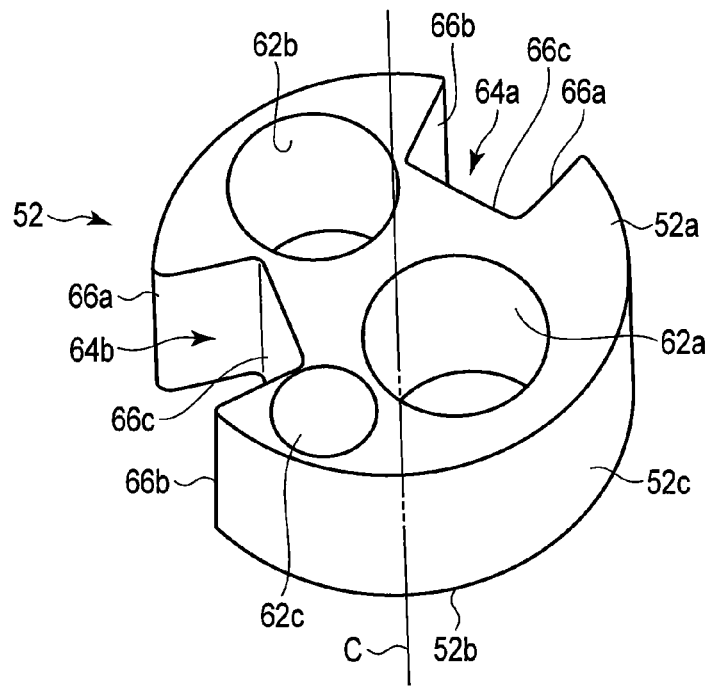
F I G. 4
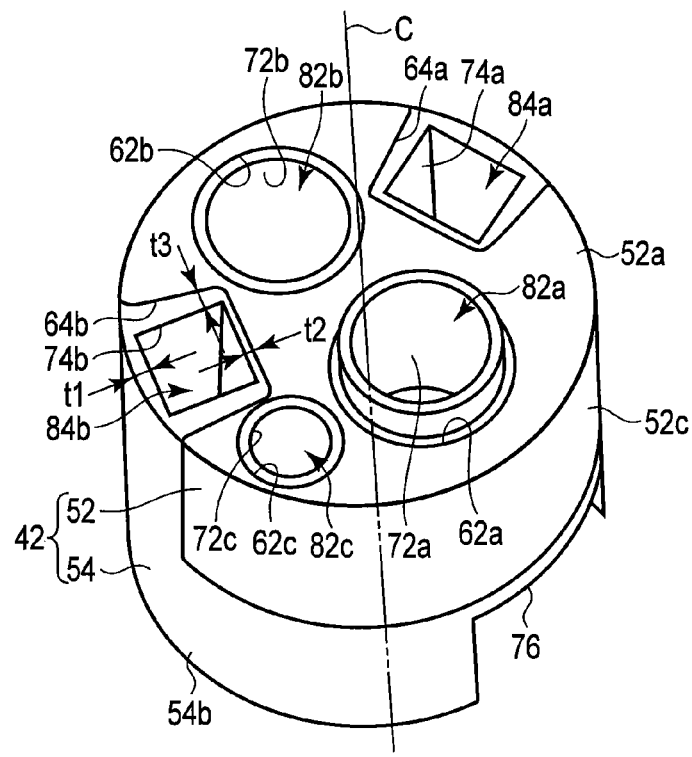
F I G. 5A

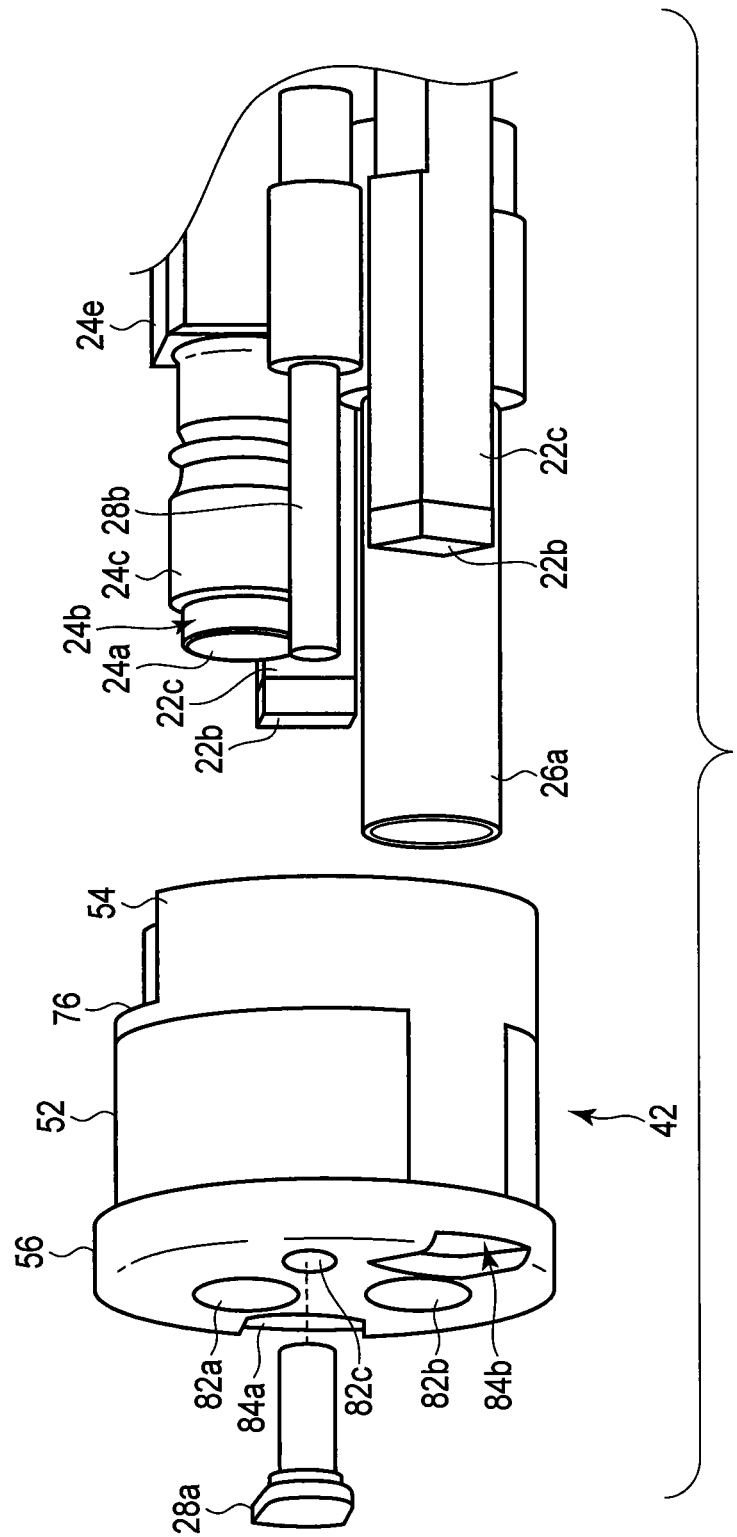
F I G. 6A

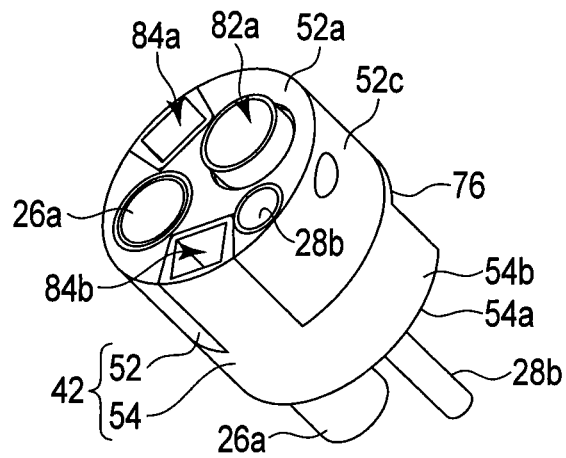
F I G. 7A
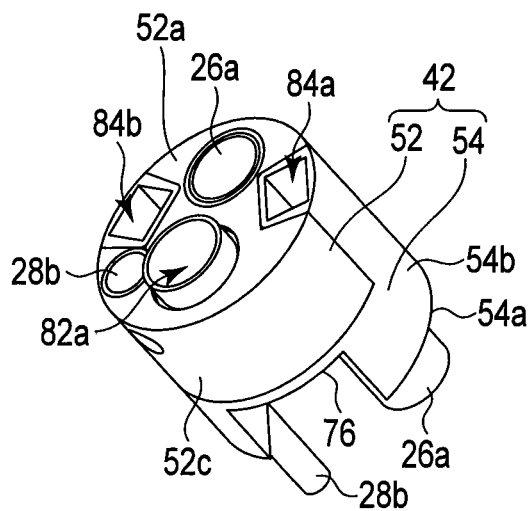
F I G. 7B

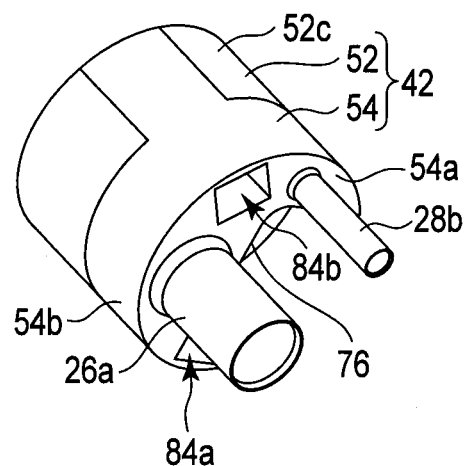
F I G. 7C
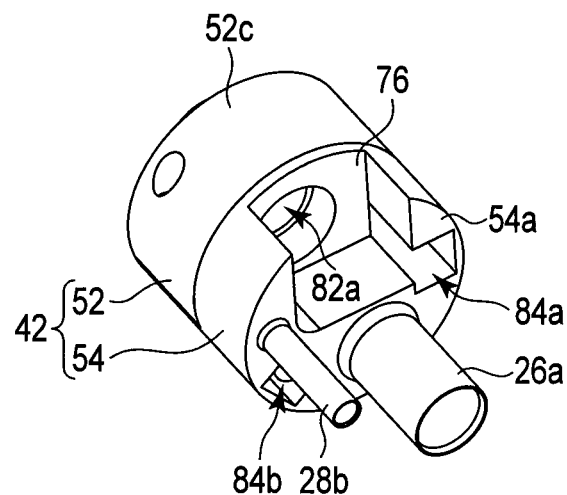
F I G. 7D

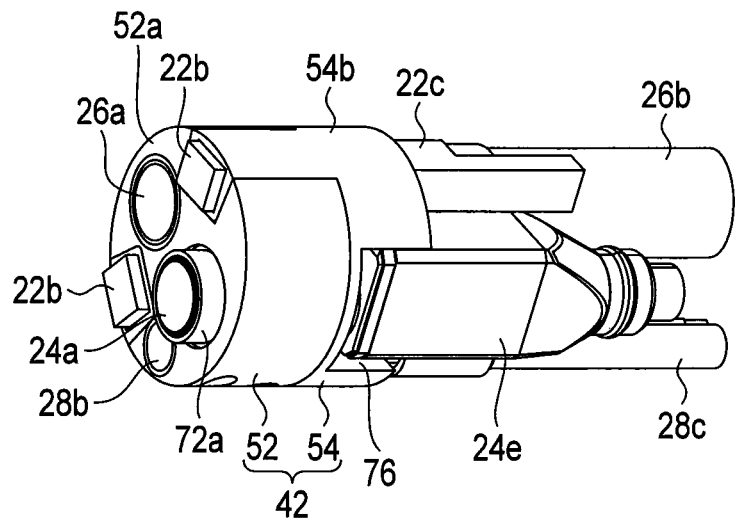
F I G. 9A
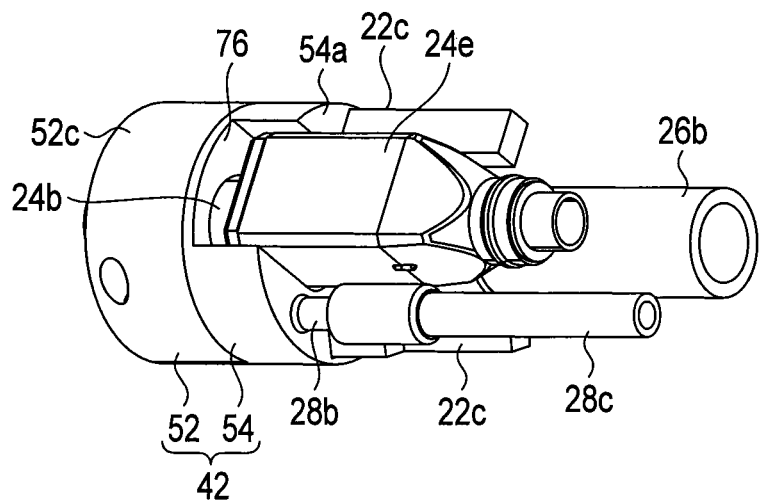
F I G. 9B

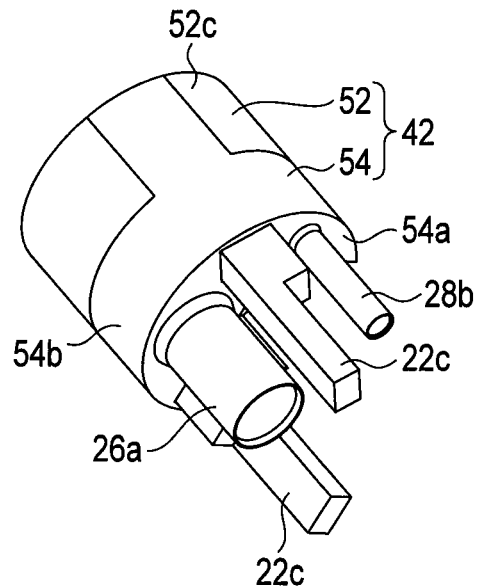
F I G. 10C
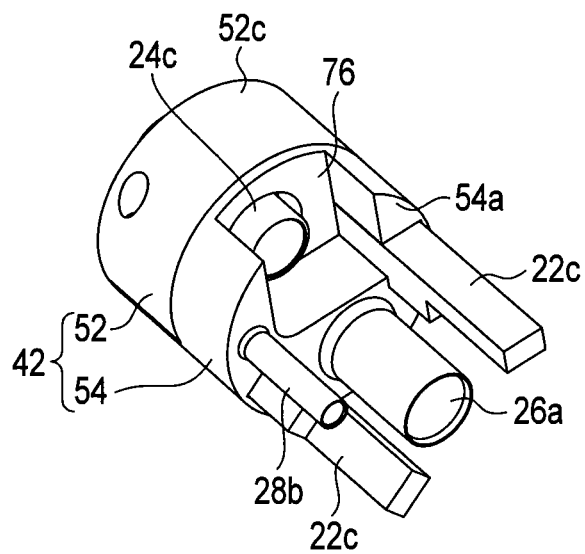
F I G. 10D

DISTAL END RIGID SECTION OF INSERTION PORTION OF ENDOSCOPE AND ENDOSCOPE

CROSS-REFERENCE TO RELATED APPLICATIONS

This application is a Continuation Application of PCT Application No. PCT/JP2013/063821, filed May 17, 2013 and based upon and claiming the benefit of priority from prior Japanese Patent Application No. 2012-160506, filed Jul. 19, 2012, the entire contents of all of which are incorporated herein by reference.

BACKGROUND OF THE INVENTION

1. Field of the Invention

The present invention relates to a distal-end rigid section of an insertion section of an endoscope, and an endoscope using the distal-end rigid section.

2. Description of the Related Art

In general, a distal-end rigid section of an insertion section of an endoscope is formed such that a distal-end portion main body, which is formed of a metallic material such as stainless steel, is coated with a cover having an insulation property. In this case, various parts are fixed by, for example, adhesion, to the distal-end portion main body and the cover of the distal-end rigid section.

BRIEF SUMMARY OF THE INVENTION

One aspect of a distal-end rigid section of an insertion section of an endoscope according to the present invention includes: a first base of a metallic material, which constitutes a distal-end portion of the insertion section of the endoscope; a second base of a resin material, which is formed on an axially proximal-end side of the first base; a cylindrical portion protruding from the second base toward an axially distal-end side of the first base and including a non-circular hole portion in which an illumination light source having a non-circular outer shape, generating light and emitting illumination light is disposed; and a through-hole formed by opening a part along an outer peripheral surface of the first base, the cylindrical portion being disposed in the through-hole such that the illumination light is emitted to the axially distal-end side of the first base.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic perspective view illustrating a first base of the distal-end rigid section of the insertion section in the endoscope according to the first to third embodiments.

FIG. 5A is a schematic perspective view illustrating a distal-end side of the distal-end rigid section including the first base and a second base of the insertion section in the endoscope according to the first to third embodiments.

FIG. 6A is a schematic perspective view illustrating, from the distal-end side, a state immediately before members constituting distal ends of illumination optical systems, an observation optical system, a channel and an air-feed/water-feed conduit (fluid conduit) are attached to the distal-end rigid section of the insertion section in the endoscope according to the first embodiment, or a state immediately after these members are removed from the distal-end rigid section at a time of repair.

FIG. 7A is a schematic perspective view illustrating, from the distal-end side, a state in which a channel pipe and an AW pipe are attached to the distal-end rigid section of the endoscope according to the second embodiment.

FIG. 7B is a schematic perspective view illustrating, from the distal-end side, the state in which the channel pipe and AW pipe are attached to the distal-end rigid section of the endoscope according to the second embodiment.

FIG. 7C is a schematic perspective view illustrating, from the proximal-end side, the state in which the channel pipe and AW pipe are attached to the distal-end rigid section of the endoscope according to the second embodiment.

FIG. 7D is a schematic perspective view illustrating, from the proximal-end side, the state in which the channel pipe and AW pipe are attached to the distal-end rigid section of the endoscope according to the second embodiment.

FIG. 9A is a schematic perspective view illustrating, from the distal-end side, a state in which the members constituting the distal ends of the illumination optical systems and observation optical system, as well as the channel tube and AW tube, have been attached to the distal-end rigid section to which the channel pipe and AW pipe are fixed; the distal-end rigid section being included in the insertion section of the endoscope according to the second embodiment.

FIG. 9B is a schematic perspective view illustrating, from the proximal-end side, the state in which the members constituting the distal ends of the illumination optical systems and observation optical system, as well as the channel tube and AW tube, have been attached to the distal-end rigid section to which the channel pipe and AW pipe are fixed, the distal-end rigid section being included in the insertion section of the endoscope according to the second embodiment.

FIG. 10C is a schematic perspective view illustrating, from the distal-end side, the state in which the small-sized light sources of the illumination optical systems, the lens frame of the observation optical system, the channel tube, and the AW tube have been attached to the distal-end rigid section of the endoscope according to the third embodiment.

FIG. 10D is a schematic perspective view illustrating, from the distal-end side, the state in which the small-sized light sources of the illumination optical systems, the lens frame of the observation optical system, the channel tube, and the AW tube have been attached to the distal-end rigid section of the endoscope according to the third embodiment.

DETAILED DESCRIPTION OF THE INVENTION

Embodiments for carrying out the invention will now be described with reference to the drawings.

A first embodiment is described with reference to FIG. 1A to FIG. 6B.

Figure 1A:
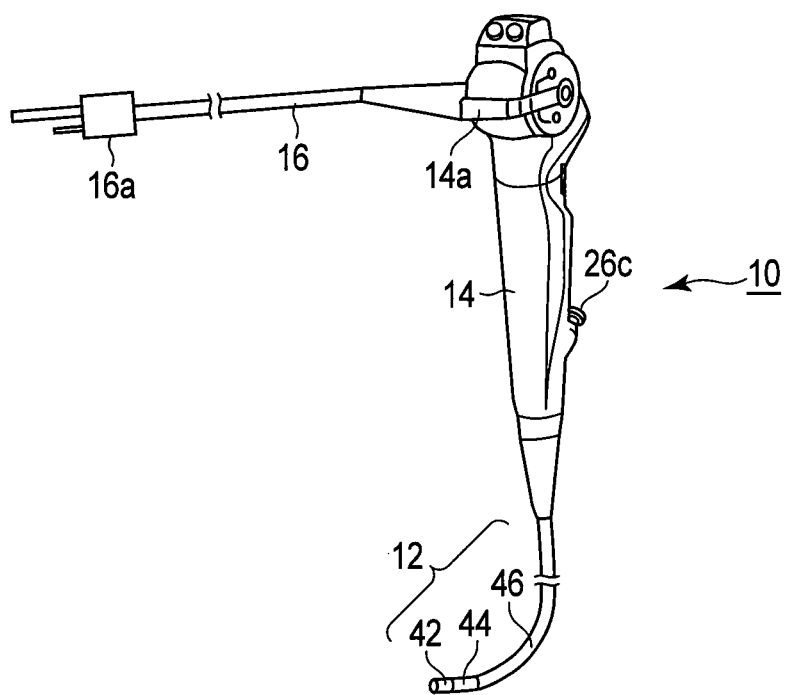
FIG. 1A is a schematic view illustrating an endoscope according to first to third embodiments.

As illustrated in FIG. 1A, an endoscope 10 includes an insertion section 12 which is inserted in, for example, tubes and cavities, such as body cavities, an operation section 14 which is held by a user, and a universal cable 16 which is extended from the operation section 14 and has a connector 16a, which is connected to a processor (not shown), at a distal end portion thereof relative to the operation section 14. In a case where the endoscope 10 according to this embodiment is for medical use, the insertion section 12 is inserted in a body cavity of a patient, and the operation section 14 is held by a surgeon and used for properly moving the insertion section 12.

Figure 2:
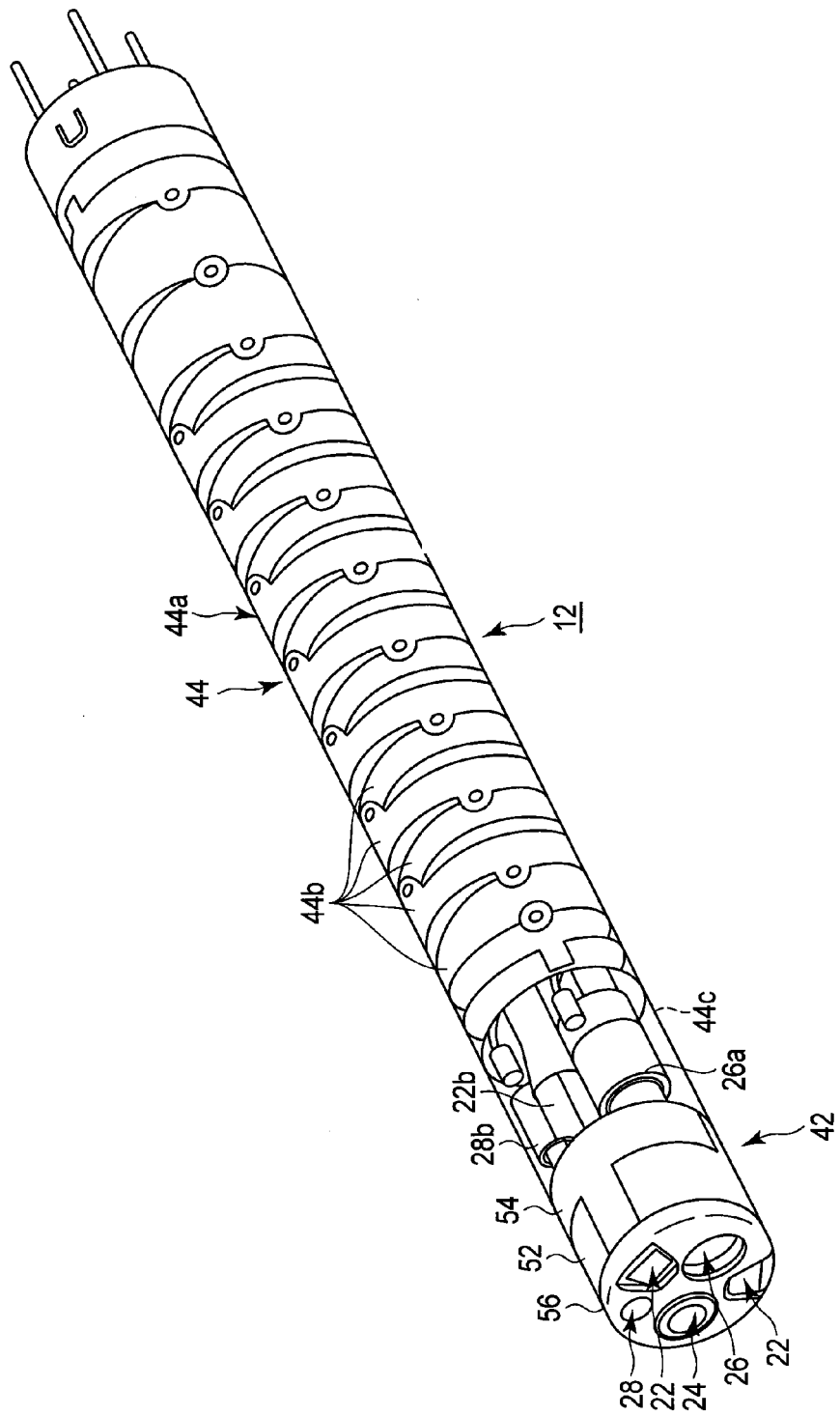
FIG. 2 is a schematic view illustrating structures of a distal-end rigid section and a bending portion of the insertion section in the endoscope according to the first to third embodiments.

The insertion section 12 is formed in a tubular shape and, as illustrated in FIG. 2, for example, a pair of illumination optical systems 22, an observation optical system 24, a channel 26, and an air-feed/water-feed conduit (fluid conduit) 28 are inserted through the insertion section 12. In the inside of the insertion section 12, publicly known components, which are not illustrated in detail, are used for the illumination optical systems 22, observation optical system 24, channel 26 and air-feed/water-feed conduit (fluid conduit) 28.

Figure 3A:
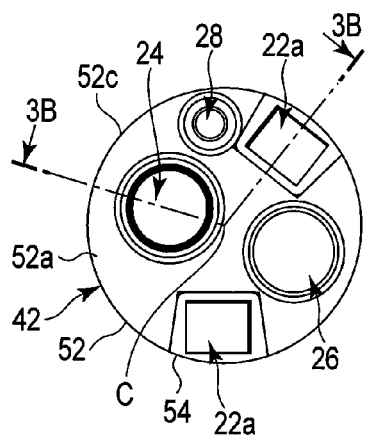
FIG. 3A is a schematic front view of the distal-end rigid section of the insertion section in the endoscope according to the first to third embodiments.
Figure 3B:
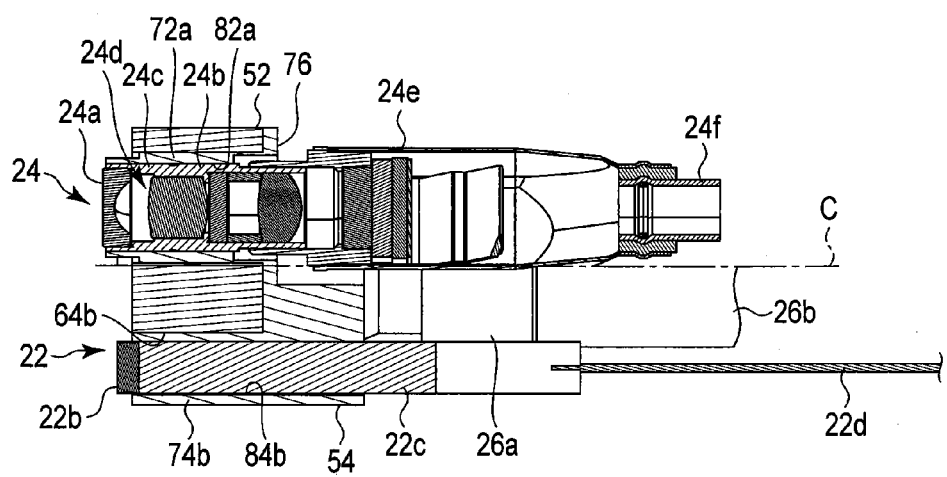
FIG. 3B is a schematic longitudinal cross-sectional view taken along line 3B-3B in FIG. 3A.

As illustrated in FIG. 3A and FIG. 3B, the illumination optical system 22 includes, at a distal end of the insertion section 12, for example, an illumination window (illumination lens) 22a, a small-sized light source (illumination light source) 22b such as an LED, a small-sized light source board 22c, and a pair of lead wires 22d which are connected to the connector 16a, and which illuminates a subject. The small-sized light source board 22c serves to connect the light source 22b and the lead wires 22d.

The observation optical system 24 includes an observation window (objective lens) 24a at the distal end of the insertion section 12, and observes the subject. The channel 26 includes a channel pipe 26a at the distal end of the insertion section 12. A therapeutic device or the like is inserted in the channel 26, and the channel 26 is also used as a suction conduit. The air-feed/water-feed conduit (fluid conduit) 28 includes a nozzle 28a at the distal end of the insertion section 12, and feeds a cleaning liquid (e.g. physiological saline), compressed air, etc. to the observation window 24a.

The illumination optical systems 22 are extended from the illumination windows 22a toward the operation section 14, the observation optical system 24 is extended from the observation window 24a toward the operation section 14, the channel 26 is extended from the channel pipe 26a toward the operation section 14, and the air-feed/water-feed conduit 28 is extended from the nozzle 28a toward the operation section 14. The illumination windows 22a, observation window 24a, channel pipe 26a, and nozzle 28a are disposed in a distal-end rigid section 42 (to be described later) of the insertion section 12.

In the distal-end rigid section 42, the observation window 24a and channel pipe 26a are disposed between the paired illumination windows 22a, and the nozzle 28a is disposed adjacent to the observation window 24a. Preferably, the observation window 24a should be equidistant from the paired illumination windows 22a.

In the illumination optical system 22, the small-sized light source (light emission part) 22b, such as an LED, is disposed on a rear-end side of the illumination window 22a, and the illumination optical system 22 illuminates the subject by emitting illumination light through the illumination window 22a. The small-sized light source board 22c is coupled to the rear-end side of the small-sized light source 22b, and the pair of lead wires 22c are extended from the board 22c. Proximal ends of the lead wires 22c are connected to, for example, the connector 16a (see FIG. 1A), and power can be obtained from the processor (not shown) or the like. An outer peripheral surface of the small-sized light source board 22c is formed of a metallic material with good heat conductivity, such as copper, and can convey heat, which is produced by the small-sized light source 22b by causing the small-sized light source 22b to emit light, to the proximal end side. The small-sized light source 22b and the illumination window 22a are electrically insulated.

In the observation optical system 24, an objective lens unit 24b is disposed on the rear-end side of the observation window 24a. The objective lens unit 24b includes a lens frame 24c and a plurality of lenses 24d. An imaging unit 24e with a rectangular cross section is disposed on the rear-end side of the objective lens unit 24b. The imaging unit 24e converts light, which is taken in through the observation window 24a with use of the objective lens unit 24b, to an electric signal. On the rear-end side of the imaging unit 24e, an imaging cable 24f is extended. A proximal end of the imaging cable 24f is connected to, for example, the connector 16a. The imaging cable 24f obtains power from the processor (not shown) or the like, and transmits the electric signal. Thus, an observed image can be displayed on a monitor (not shown).

Figure 1B:
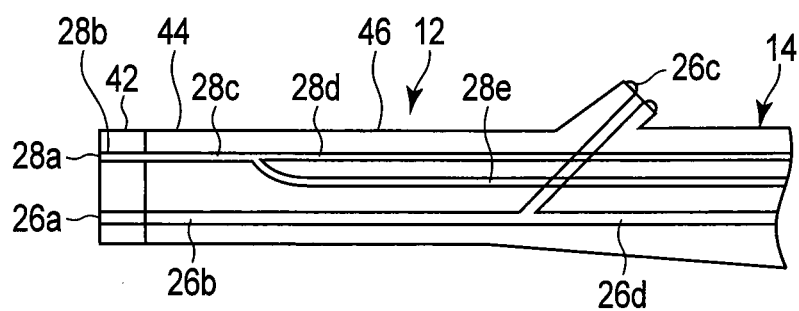
FIG. 1B is a schematic pattern diagram illustrating a part of internal structures of an insertion section and an operation section in FIG. 1A.

As illustrated in FIG. 1B, in the insertion section 12, the channel 26 is configured such that a channel tube 26b is disposed on the rear-end side of the channel pipe 26a. A proximal end of the channel tube 26b is connected to a forceps hole 26c which is provided in the operation section 14. Thus, a therapeutic device can be projected at the distal-end surface of the distal-end rigid section 42 (to be described later) through the channel 26b and channel pipe 26a from the forceps hole 26c. It should be noted that, as is publicly known, the channel 26 can be used as a part of a suction conduit 26d.

In the fluid conduit 28, at the proximal end of the nozzle 28a, for example, a pipe (hereinafter referred to as "AW pipe") 28b, which is formed of stainless, steel and feeds air and physiological saline, and a tube (hereinafter referred to as "AW tube") 28c, which has flexibility and feeds air and physiological saline, are disposed in order from the distal-end side toward the proximal-end side. Furthermore, the AW tube 28c is branched into two flow paths at the proximal-end side, namely a flow path 28d of physiological saline, and a flow path 28e of a gas (air). These flow paths 28d and 28e can discharge physiological saline or air toward the observation window 24a from the nozzle 28a by a publicly known mechanism.

As illustrated in FIG. 1A, the insertion section 12 includes a distal-end rigid section 42, a bending portion 44, and a tubular body 46 in the named order from the distal-end portion of the insertion section 12 (the distal side relative to the operation section 14) toward the proximal-end portion (toward the operation section 14 side). A so-called flexible tube illustrated in FIG. 1A may be used for the tubular body 46, or a rigid pipe (not shown), which hardly deforms even when a force is applied, may be used for the tubular body 46. In the case of using the rigid pipe, use is made of a metallic material such as stainless steel, or a plastic material such as a reinforced resin. FIG. 1A illustrates an example in which the flexible tube is used for the tubular body 46 of the insertion section 12 of the endoscope 10.

As illustrated in FIG. 2, the bending portion 44 includes a bending tube 44a in which, for example, a plurality of publicly-known bend pieces 44b are juxtaposed in the axial direction of the insertion section 12. Neighboring bend pieces 44b are rotatable relative to each other. A distal end of a wire is fixed to the foremost distal-end-side bend piece 44b, and the wire is successively passed through the bend pieces neighboring on the proximal-end side. A proximal end of the wire is extended, for example, to the operation section 14 through the tubular body 46. If the surgeon operates a knob 14a of the operation section 14 and moves the wire in its axial direction, the bending portion 44 can properly be bent.

Distal-end structural parts of the illumination optical systems 22, observation optical system 24, channel 26, and air-feed/water-feed conduit 28 are fixed to the distal-end rigid section 42.

Figure 5B:
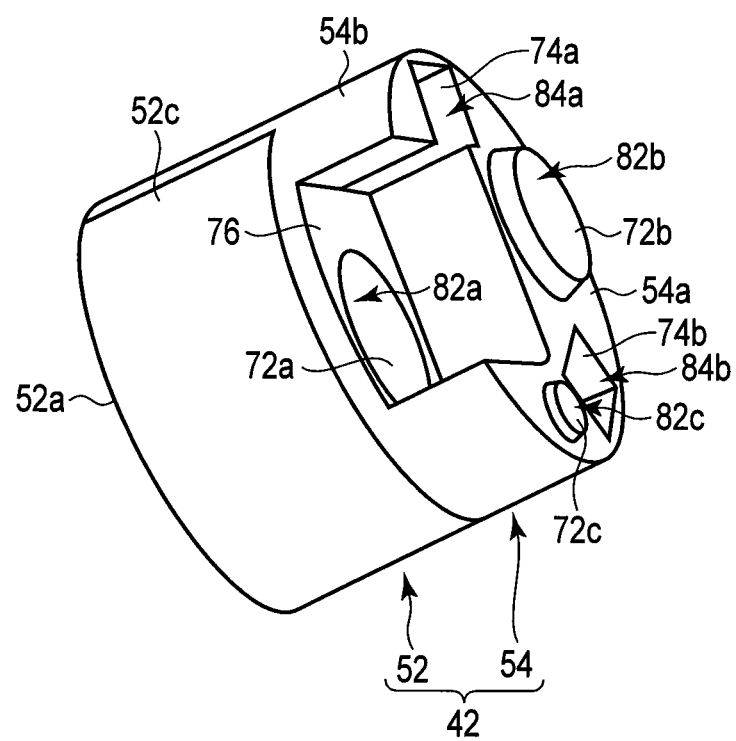
FIG. 5B is a schematic perspective view illustrating a proximal-end side of the distal-end rigid section including the first base and second base of the insertion section in the endoscope according to the first to third embodiments.

As illustrated in FIG. 4 to FIG. 5B, the distal-end rigid section 42 includes a first base 52 which is formed of a metallic material, and a second base 54 which is formed of a resin material so as to be made integral as one piece with the first base 52 of the metallic material. The first base 52 is formed of the metallic material so as to maintain the rigidity of the distal-end rigid section 42. For instance, a stainless alloy, an aluminum alloy, a magnesium alloy, or a titanium alloy can be used for the first base 52 of the metallic material.

As illustrated in FIG. 4, the first base 52 is formed in a substantially columnar shape, and has a distal-end surface 52a, a proximal-end surface 52b, and an outer peripheral surface 52c. It is preferable that the distal-end surface 52a and proximal-end surface 52b be parallel planar surfaces, in order to ensure the ease of processing the first base 52.

The first base 52 includes circular through-holes 62a, 62b, and 62c penetrating in the axial direction of the insertion section 12 (the direction along a center axis C in FIG. 4), that is, penetrating from the distal-end surface 52a to the proximal-end surface 52b, and non-circular through-holes 64a and 64b which are juxtaposed with the circular through-holes 62a, 62b, and 62c and are accessible to the outer peripheral surface 52c of the first base 52. It should suffice if there is any one of the circular through-holes 62a, 62b, and 62c, and if there is, for example, one of the non-circular through-holes 64a and 64b. The non-circular through-holes 64a and 64b have opposed surfaces 66a and 66b, and a surface 66c which connects the opposed surfaces 66a and 66b, and is formed in a substantially rectangular shape by opening a part along the outer peripheral surface 52c. A circumferential distance between the opposed surfaces 66a and 66b of the non-circular through-holes 64a and 64b is set to become gradually smaller on a side near the center axis C than on the outer peripheral surface 52c side. Thus, the circumferential opening width of the non-circular through-holes 64a and 64b becomes gradually smaller from the outer peripheral surface 52c side toward the center axis C. Specifically, the opposed surfaces 66a and 66b of the non-circular through-holes 64a and 64b are formed in such a tapered shape as to be narrower on the side near the center axis C of the first base 52 than on the outer peripheral surface 52c of the first base 52.

As illustrated in FIG. 5A and FIG. 5B, the second base 54 is formed of a resin material in order to fix members which are disposed at the distal ends of the illumination optical systems 22, observation optical system 24, channel 26, and air-feed/water-feed conduit 28, to ensure insulation between these members and the first base 52, and to prevent as much as possible the radiation of heat from the distal-end rigid section 42. It is preferable that the second base 54 be formed of, for example, a crystalline resin material among rigid resin materials. As the resin material of the second base 54, for example, use is made of PPS, PPA, etc. The endoscope 10 is exposed to high temperatures at a time of performing cleaning or sterilization. It is thus preferable that a small amount of carbon fibers or glass fibers be mixed in the resin material of the second base 54, so that the linear expansion coefficient of the second base 54 is made closer to that of the first base 52.

Although it is necessary that the first base 52 and second base 54 be coupled with high strength and watertightness, there are various publicly-known techniques for coupling a metallic material and a resin material with high strength and watertightness, and these techniques can be properly used.

The second base 54 is airtightly and watertightly formed as one piece with the first base 52 on the axially proximal-end side of the first base 52. The second base 54 airtightly and watertightly covers inner peripheral surfaces of the circular through-holes 62*a*, 62*b*, and 62*c* from the first base 52. Thus, in the distal-end rigid section 42, circular-cylindrical portions 72*a*, 72*b*, and 72*c* are formed by the second base 54. In addition, the second base 54 airtightly and watertightly covers inner peripheral surfaces of the non-circular through-holes 64*a* and 64*b* from the first base 52. Thus, in the distal-end rigid section 42, cylindrical portions 74*a* and 74*b* are formed by the second base 54. In addition, in the second base 54, a recess portion 76, which communicates with the circular-cylindrical portion 72*a* and is open to a proximal-end surface 54*a* and an outer peripheral surface 54*b*, is formed.

It should be noted that it is preferable that the outer peripheral surface 52*c* of the first base 52 and the outer peripheral surface 54*b* of the second base 54 be formed flush with each other.

In the present embodiment, as illustrated in FIG. 3B and FIG. 5A, a distal end of the circular-cylindrical portion 72*a* of the second base 54, in which the observation optical system 24 is disposed, is located at a position projecting toward the distal-end side, relative to the distal-end surface 52*a* of the first base 52. Distal ends of the circular-cylindrical portions 72*b* and 72*c* of the second base 54, in which the channel 26 and air-feed/water-feed conduit 28 are disposed, and distal ends of the cylindrical portions 74*a* and 74*b*, in which the illumination optical systems 22 are disposed, are located to be flush with the distal-end surface 52*a* of the first base 52, or to be slightly recessed toward the proximal-end side. In addition, as illustrated in FIG. 3B and FIG. 5B, a proximal end of the circular-cylindrical portion 72*a* of the second base 54, in which the observation optical system 24 is disposed, communicates with the recess portion 76 of the second base 54. Proximal ends of the circular-cylindrical portions 72*b* and 72*c* of the second base 54, in which the channel 26 and air-feed/water-feed conduit 28 are disposed, are located to be flush with the proximal-end surface 54*a* of the second base 54, or to slightly project toward the proximal-end side. Furthermore, proximal ends of the circular-cylindrical portions 74*a* and 74*b* of the second base 54, in which the illumination optical systems 22 are disposed, are located to be flush with the proximal-end surface 54*a* of the second base 52.

The positions and shapes of the circular-cylindrical portions 72*a*, 72*b*, and 72*c* and cylindrical portions 74*a* and 74*b*, relative to the distal-end surface 52*a* of the first base 52, can be properly set since these portions are formed of the resin material. In addition, the positions and shapes of the circular-cylindrical portions 72*a*, 72*b*, and 72*c* and cylindrical portions 74*a* and 74*b*, relative to the proximal end of the second base 54, can also be properly set.

As illustrated in FIG. 5A, the cylindrical portions 74*a* and 74*b* of the second base 54, which cover the non-circular through-holes 64*a* and 64*b* of the first base 52, are formed such that a radial thickness t1 thereof on the outer peripheral surface 52*c* side of the first base 52 is greater than a radial thickness t2 thereof on the center axis C side of the first base 52. In addition, the cylindrical portions 74*a* and 74*b* of the second base 54 are formed such that a circumferential thickness t3 thereof on the side of the opposed surfaces 66*a* and 66*b* of the non-circular through-holes 64*a* and 64*b* is greater than the radial thickness t2 on the center axis C side. Therefore, when heat is transferred from the small-sized light sources 22*b* of the illumination optical systems 22 via the second base 54, the heat is made to converge at a position closer to the heat sources, that is, more on the center axis C side than on the outside of the first base 52. Thus, although it is considered that the outer peripheral surface 52*c* of the first base 52 of the distal-end rigid section 42 comes in contact with living tissue more easily than the distal-end surface 52*a* thereof when the insertion section 12 is being inserted into, e.g. a body cavity, it becomes possible to prevent as much as possible the heat that is produced from the small-sized light sources 22*b* from being radiated to the outside at a position near the outer peripheral surface 52*c* of the first base 52 of the distal-end rigid section 42.

Regarding the thickness of each of the circular-cylindrical portions 72*a*, 72*b*, and 72*c* and the cylindrical portions 74*a* and 74*b* of the second base 54, it should suffice if electrical insulation can be ensured between the first base 52 and the members disposed inside the circular-cylindrical portions 72*a*, 72*b*, and 72*c* and the cylindrical portions 74*a* and 74*b* of the second base 54. Thus, for example, the circular-cylindrical portions 72*a*, 72*b*, and 72*c* of the second base 54 may have a thin-film shape.

Accordingly, in the distal-end rigid section 42, first to third hole portions 82*a*, 82*b*, and 82*c* are formed by the cooperation between the circular through-holes 62*a*, 62*b*, and 62*c* of the first base 52 and the circular-cylindrical portions 72*a*, 72*b*, and 72*c* of the second base 54, and fourth and fifth hole portions 84*a* and 84*b* are formed by the cooperation between the non-circular through-holes 64*a* and 64*b* of the first base 52, and the cylindrical portions 74*a* and 74*b* of the second base 54. Specifically, the distal-end rigid section 42 includes the first hole portion 82*a* in which the observation window 24*a* and objective lens unit 24*b* of the observation optical system 24 are disposed, the second hole portion 82*b* in which the channel pipe 26*a* is disposed, and the third hole portion 82*c* in which the nozzle 28*a* of the fluid conduit 28 is disposed, in the state in which these hole portions penetrate the distal-end rigid section 42. The distal-end rigid section 42 further includes the fourth hole portion 84*a* and fifth hole portion 84*b* for disposing therein the illumination windows 22*a* and small-sized light sources 22*b* of the illumination optical systems 22.

Therefore, as illustrated in FIG. 5B, the second base 54 includes, on the proximal-end side thereof, the substantially rectangular recess portion 76, which is continuous with the circular-cylindrical portion 72*a* of the second base 54 and in which the imaging unit 24*e* of the observation optical system 24 is engaged. Since the second base 54 is formed of resin material, the rectangular recess portion 76 can easily be formed. Thus, an outer peripheral surface with a rectangular cross section of the imaging unit 24*e* can be engaged with the recess portion 76 of the second base 54. In addition, the lens frame 24*c* can be disposed in the circular-cylindrical portion 72*a*, that is, the first hole portion 82*a*, through the rectangular recess portion 76 of the second base 54.

In the present embodiment, as illustrated in FIG. 5A, on the distal-end side of the distal-end rigid section 42, the ratio of exposure of the first base 52 is greater than the ratio of exposure of the second base 54, and, as illustrated in FIG. 5B, on the proximal-end side, the ratio of exposure of the second base 54 is greater than the ratio of exposure of the first base 52. In this case, the entirety of the proximal-end side of the distal-end rigid section 42 is formed of the second base 54.

A distal-end cover (distal-end insulation layer) 56 is attachable to and detachable from the distal-end rigid section 42 of the endoscope 10 according to this embodiment. The distal-end cover 56 protects the distal-end surface 52a and the outer peripheral surface 52c of the first base 52. In this embodiment, the distal-end cover 56 is formed in a substantially circular-cylindrical shape of a resin material such as polysulfone with heat resistance, electrical insulation properties, and acid resistance and base resistance.

Part of the outer peripheral surface 52c of the first base 52 and the outer peripheral surface 54b of the second base 54 are covered with an outer sheath 44c.

Next, the operation of the endoscope 10 according to this embodiment is described.

The first base 52 and second base 54 are made integral as one piece, thus preparing the distal-end rigid section 42 including the first to fifth hole portions 82a, 82b, 82c, 84a, and 84b, and the recess portion 76. At this time, if necessary, the insulative cover 56, which can cover the distal-end surface 52a and the distal-end side of the outer peripheral surface 52c of the first base 52 of the distal-end rigid section 42, is prepared.

In the state in which the illumination optical systems 22, observation optical system 24, channel 26, and air-feed/water-feed conduit (fluid conduit) 28 are passed through a helical tube (not shown) of the tubular body 46 and the bending tube 44a (see FIG. 2) of the bending portion 44 of the insertion section 12, the distal-end structural members of the illumination optical systems 22, observation optical system 24, channel 26, and air-feed/water-feed conduit 28 are projected from the distal end of the bending tube 44a. Thus, as illustrated in FIG. 6A and FIG. 6B, the distal-end structural members of the illumination optical systems 22, observation optical system 24, channel 26, and air-feed/water-feed conduit 28 are opposed to the proximal-end side of the second base 54 of the distal-end rigid section 42.

Figure 6B:
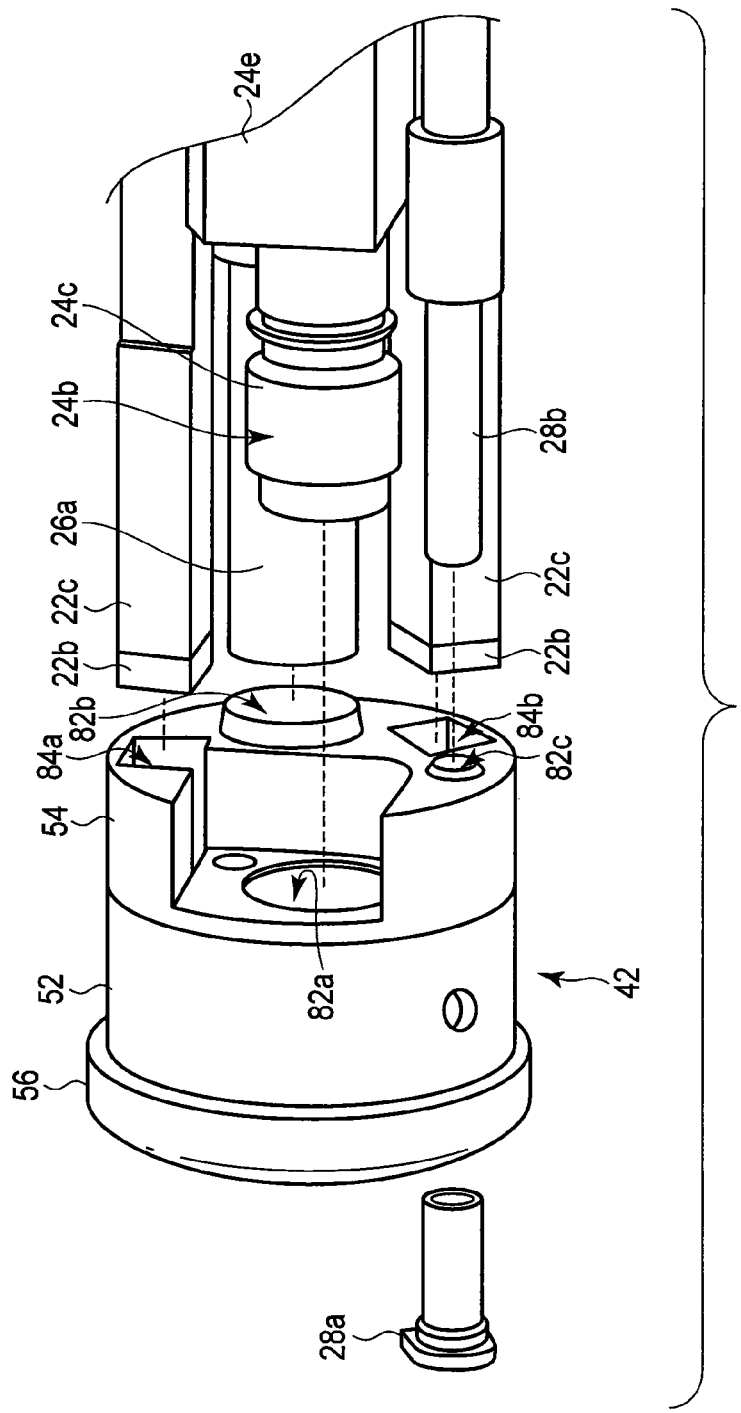
FIG. 6B is a schematic perspective view illustrating, from the proximal-end side, the state immediately before the members constituting the distal ends of the illumination optical systems, observation optical system, channel, and air-feed/water-feed conduit (fluid conduit) are attached to the distal-end rigid section of the insertion section in the endoscope according to the first embodiment, or the state immediately after these members are removed from the distal-end rigid section at a time of repair.

As illustrated in FIG. 6A and FIG. 6B, the observation window 24a, objective lens unit 24b, imaging unit 24e, and imaging cable 24f are integrated as one piece. In this state, the imaging unit 24e is engaged in the recess portion 76 of the second base 54, and the lens frame 24c, in which the observation window 24a and lenses 24d of the observation optical system 24 are disposed, is disposed in the circular first hole portion 82a. At this time, the lens frame 24c is fixed by a pin (not shown) or the like from the outer peripheral surfaces 52c and 54b of the first base 52 or second base 54. Then, an adhesive is applied to achieve airtightness and watertightness between the outer peripheral surface of the lens frame 24c and the distal end of the first hole portion 82a.

The channel pipe 26a and channel tube 26b are integrated as one piece. The channel pipe 26a is disposed in the second hole portion 82b, and the channel pipe 26a is fixed by a pin (not shown) or the like from the outer peripheral surfaces 52c and 54b of the first base 52 or second base 54. Then, an adhesive is applied to achieve airtightness and watertightness between the outer peripheral surface of the channel pipe 26a and the distal end of the second hole portion 82b.

The AW pipe 28b and AW tube 28c of the fluid conduit are integrated as one piece. In the third hole portion 84c, the nozzle 28a is disposed from the first base 52 side via the cover 56, and the AW pipe 28b is disposed. The nozzle 28a and AW pipe 28b are fixed by a pin (not shown) or the like from the outer peripheral surfaces 52c and 54b of the first base 52 or second base 54. At this time, an adhesive is applied to achieve airtightness and watertightness between the outer peripheral surface of the nozzle 28a and the distal end of the third hole portion 82c, and an adhesive is applied to achieve airtightness and watertightness between the outer peripheral surface of the AW pipe 28b and the third hole portion 82c.

The small-sized light source 22b, small-sized light source board 22c, and lead wires 22d (see FIG. 6A and FIG. 6B) are integrated as one piece. The small-sized light source 22b and small-sized light source board 22c, each having a rectangular cross section, are disposed in each of the rectangular fourth and fifth hole portions 84a and 84b, and the small-sized light source 22b is fixed by a pin (not shown) or the like from the outer peripheral surfaces 52c and 54b of the first base 52 or second base 54. At this time, the proximal end of the small-sized light source 22b may be located on the same plane as the distal end of the first base 52. Specifically, of the small-sized light source 22b and light source board 22c, only the small-sized light source board 22c (at least one of the small-sized light source 22b and small-sized light source board 22c) may be disposed in each of the rectangular fourth and fifth hole portions 84a and 84b. Then, an adhesive is applied to achieve airtightness and watertightness between the outer peripheral surfaces of the small-sized light source 22b and small-sized light source board 22c and the distal end of each of the fourth and fifth hole portions 84a and 84b.

It should be noted that the pin (not shown) or the like may be used as needed, or may be made unnecessary.

If necessary, of the distal-end rigid section 42, the distal-end surface 52a and outer peripheral surface 52c of the first base 52 can be covered with the insulative cover 56.

At this time, the insertion section 12 of the endoscope 10 is in the state as illustrated in FIG. 2. The outside of the bending portion 44 is covered with the outer sheath 44c. The outer sheath 44c covers not only the outside of the bending portion 44, but also the outer peripheral surface 54b of the second base 54 of the distal-end rigid section 42, and the outer peripheral surface 52c of the first base 52. Then, a process is performed to ensure watertightness between the proximal end of the cover 56 and the distal end of the outer sheath 44. Specifically, in this embodiment, the outer peripheral surface of the distal-end rigid section 42 is coated with an insulator by the cover 56 and the outer sheath 44c.

In this case, since the heat capacity of the resin material is lower than that of the metallic material, heat is transferred less easily through the resin material than through the metallic material. If power is supplied to the illumination optical systems 22 via the connector 16a of the endoscope 10, the small-sized light sources 22b emit light. At this time, heat is produced in accordance with the emission of light by the small-sized light source 22b. The outer peripheral surface of the small-sized light source 22b is formed of the metallic material, and functions as a heat transfer part. Specifically, the heat, which is produced in accordance with the light emission of the small-sized light source 22b, is transferred to the proximal-end side of the illumination optical system 22 (the side toward the connector 16) via the outer peripheral surface of the small-sized light source board 22c, and is gradually radiated. In addition, when the heat by the small-sized light source 22b is also transferred to the first base 52 via the second base 54, the heat is conveyed to the center axis C side of the first base 52. Therefore, it is possible to prevent the heat from the light source 22b from being radiated toward the outer peripheral surface of the distal-end rigid section 42.

In the case of repairing the endoscope 10, since the illumination optical systems 22, observation optical system 24, channel 26, and air-feed/water-feed conduit 28 are formed integral in the distal-end rigid section 42, the proximal-end structural members of the illumination optical systems 22, observation optical system 24, channel 26, and air-feed/water-feed conduit 28 are removed from the distal-end rigid section 42. At this time, since it should suffice if these distal-end structural members are removed from the second base 54, repair is easier than in the case where additional parts for ensuring insulation are present between the distal-end structural members and the distal-end rigid section 42.

As has been described above, according to this embodiment, the following advantageous effects can be obtained.

The first base 52 is formed in the columnar shape having the planar surfaces 52a and 52b, which are parallel to each other, and having the outer peripheral surface 52c. One or a plurality of circular through-holes 62a, 62b, and 62c, which have the axial direction perpendicular to the planar surfaces 52a and 52b, are formed. One or a plurality of non-circular through-holes 64a and 64b, which are juxtaposed with the circular through-holes 62a, 62b, and 62c, and are accessible to the outer peripheral surface 52c, are formed. The rigidity of the distal-end rigid section 42 can be maintained by the first base 52 which is formed of the metallic material in the columnar shape. Thus, the shock resistance for the distal-end rigid section 42 can be maintained. In addition, the processing for the first base 52 is easy since it should suffice if the circular through-holes 62a, 62b, and 62c are formed and the through-holes 64a and 64b, which have such shapes as to be accessible from the outer peripheral surface, are formed. Thus, the manufacturing costs of the first base 52 can be held to a minimum. In addition, by forming the second base 54 of the resin material to be integral as one piece with the first base 52 of the metallic material, the shapes of the cylindrical portions 74a and 74b having the rectangular hole portions 84a and 84b and the recess portion 76 can easily be realized by the second base 54 of the resin material. In the case of the metallic material, the processing would be difficult and the cost would increase. Therefore, the total manufacturing cost of the distal-end rigid par 42 can greatly be reduced.

For example, the shapes that are difficult to realize by a machining process, such as the shapes of the fourth and fifth hole portions 84a and 84b, and the shape of the recess portion 76 in which the rectangular imaging unit 24e is engaged, can easily be realized by the resin, that is, the second base 54. Regarding the shape of the distal-end rigid section 42, since the first base 52 of the metallic material is simply formed and the structure, which is difficult to form with the metallic material, can be easily adopted for the shape of the second base 54 of the resin material, the whole shape of the distal-end rigid section 42 can easily be formed by adopting, for example, a rectangular shape, etc. Specifically, it is possible to prevent restrictions from being imposed on the shape of the distal-end rigid section 42.

By using the technique of integrating the metallic material and resin material (plastic material), it becomes possible to realize airtightness and watertightness between the first and second bases 52 and 54, without using an adhesive between the first base 52 of the metallic material and the second base 54 of the resin material.

By forming the second base 54 of the resin, there is no need to add additional parts for insulation at the locations that require electrical insulation, and the electrical safety for the first base 52 can be ensured. Specifically, since the second base 54 with the electrical insulation property is present between the first base 52 of the metallic material and the structure units, such as the nozzle 28a and illumination optical systems 22, which require insulation from the first base 52 of the metallic material, the insulation between the first base 52 and the structure units can be ensured without using new parts.

Thus, not only at the time of manufacture but also when repairing the endoscope, there is no need to use additional parts for insulation. Therefore, the number of times of application of an adhesive can be reduced, and the efficiency in manufacturing and repairing the endoscope 10 can be enhanced.

By forming the second base 54 of the resin material, the cylindrical portions 74a and 74b can be formed in accordance with the shapes of parts. When the illumination light source 22b, such as an LED, which has a non-circular outer shape, and the small-sized light source board 22c are attached to the distal-end rigid section 42, the shapes of the fourth and fifth hole portions 84a and 84b can be formed by the second base 54 in accordance with the outer shapes of the illumination light source 22b. Thus, there is no need to do work such as filling in a resin material between the circular hole and the non-circular illumination light source 22b and small-sized light source board 22c. In addition, in general, when a part is attached to a circular hole, an outside diameter, which is equal to or greater than a maximum diagonal of the part that is to be attached, is needed, and accordingly the outside diameter of the distal-end rigid section tends to become larger. However, in this embodiment, it should suffice if the rectangular hole portions 84a and 84b with a smaller cross section than a circular hole are formed by forming the cylindrical portions 74a and 74b with a non-circular cross section such as a rectangular cross section. Thus, the outside diameter of the distal-end rigid section 42 can be reduced, and accordingly the insertion section 12 can be reduced in size. In addition, a work step such as filling a resin material in the circular hole is made unnecessary, and the efficiency in manufacture and repair of the endoscope 10 can be enhanced.

By disposing the small-sized light sources (LED units) 22b, which are exothermic sources, in the fourth and fifth hole portions 84a and 84b of the second base 54, a temperature rise at parts of the distal-end rigid section 42 can be prevented. Since the outer peripheral surface of the small-sized light source 22b is formed of the metallic material, the heat produced from the small-sized light source 22b can be caused to escape to the proximal-end side by the small-sized light source board 22c, from the distal-end rigid section 42 of the insertion section 12 toward the bending portion 44 and tubular body 46.

As has been described above, according to the distal-end rigid section 42 of the embodiment, there is little variance in quality when various parts are attached, the efficiency in manufacture and repair is high, the diameter of the insertion section 12 can be reduced even if the small-sized light source 22b, which can gain a proper light amount, is directly disposed, and the heat produced from the small-sized light source 22b can be prevented from being radiated directly to the outside.

It should be noted that in this embodiment, it has been described that the distal-end surface 52a and the distal-end side of the outer peripheral surface 52c of the first base 52 of the distal-end rigid section 42 are covered with the insulative cover 56 which is used as the insulation layer. However, it is also preferable that the distal-end cover 56 be made integral as one piece with the first base 52 together with the second base 54. In this case, for example, after the first base 52 and second base 54 are made integral, the distal-end cover 56 of the resin material, such as polysulfone, may be made integral with the first base 52 and second base 54.

In addition, in FIG. 6A and FIG. 6B, the outer peripheral surface of the distal-end cover 56 is depicted as protruding to the outside from the outer peripheral surfaces 52c and 54b of the first base 52 and second base 54. However, it is also preferable that the distal-end cover 61 have the same outside diameter as the first base 52 and second base 54. In other words, it is also preferable that the distal-end cover 56, which is used as the insulation layer, be formed flush with the outer peripheral surfaces 52c and 54b of the first base 52 and second base 54.

Next, a second embodiment is described with reference to FIG. 7A to FIG. 9B. This embodiment is a modification of the first embodiment. The parts, which are identical to, or have the same functions as, the parts described in the first embodiment, are denoted by like reference numerals when possible, and a detailed description thereof is omitted.

In this embodiment, as illustrated in FIG. 7A to FIG. 7D, the channel pipe 26a and AW pipe 28b are formed integral with the second base 54 of the distal-end rigid section 42 which has been described in the first embodiment. Specifically, in the distal-end rigid section 42 according to this embodiment, the second base 54 is formed integral with the first base 52, and the channel pipe 26a and AW pipe 28b are formed integral with the second base 54.

It should be noted that the distal end of the channel pipe 26a and the distal end of the AW pipe 28b are located to be flush with the distal-end surface 52a of the first base 52, or are located to be recessed to the proximal-end side from the distal-end surface 52a. The proximal end of the channel pipe 26a and the distal end of the AW pipe 28b are located to further extend to the proximal-end side from the proximal-end surface 54a of the second base 54.

The channel pipe 26a is fixed to the inner peripheral surface of the circular-cylindrical portion 72b of the second base 54, and the AW pipe 28b is fixed to the inner peripheral surface of the circular-cylindrical portion 72c of the second base 54. Thus, electrical insulation is achieved between the channel pipe 26a and the first base 52 and between the AW pipe 28b and the first base 52.

Figure 8A:
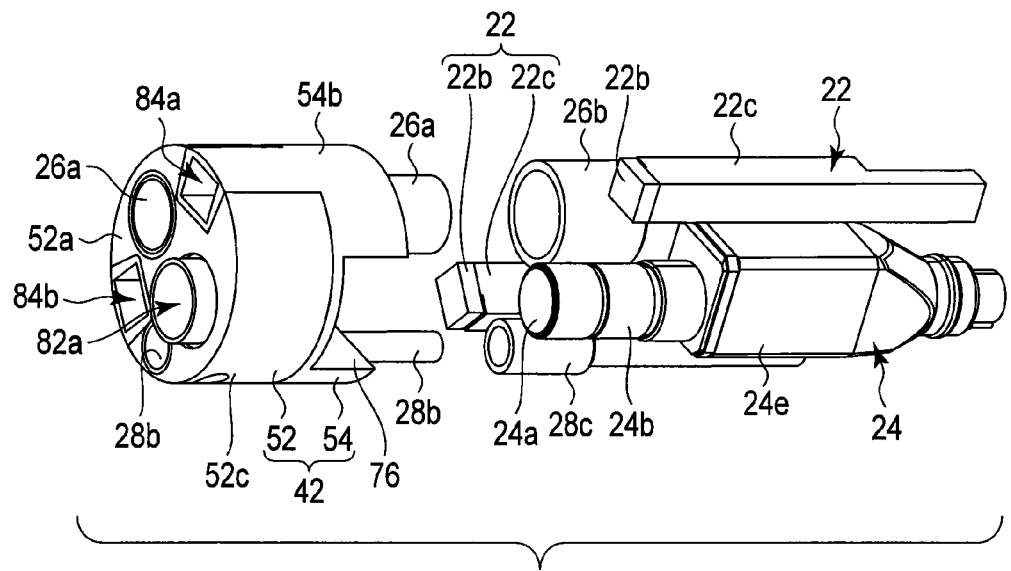
FIG. 8A is a schematic perspective view illustrating, from the distal-end side, a state immediately before the members constituting the distal ends of the illumination optical systems and observation optical system, as well as a channel tube and an AW tube, are attached to the distal-end rigid section to which the channel pipe and AW pipe are fixed, the distal-end rigid section being included in the insertion section of the endoscope according to the second embodiment, or a state immediately after these members, channel tube, and AW tube are removed from the distal-end rigid section at a time of repair.
Figure 8B:
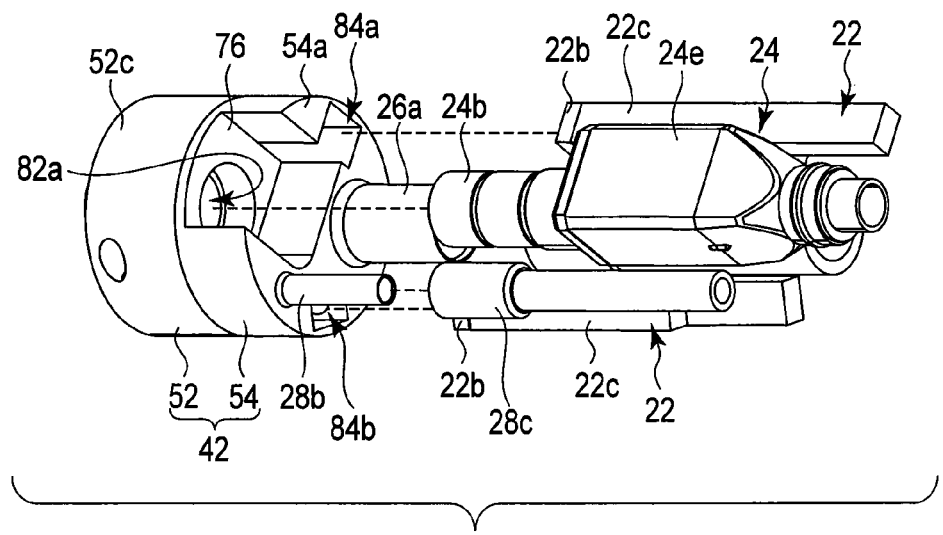
FIG. 8B is a schematic perspective view illustrating, from the proximal-end side, the state immediately before the members constituting the distal ends of the illumination optical systems and observation optical system, as well as the channel tube and AW tube, are attached to the distal-end rigid section to which the channel pipe and AW pipe are fixed, the distal-end rigid section being included in the insertion section of the endoscope according to the second embodiment, or the state immediately after these members, channel tube, and AW tube are removed from the distal-end rigid section at a time of repair.
Figure 10A:
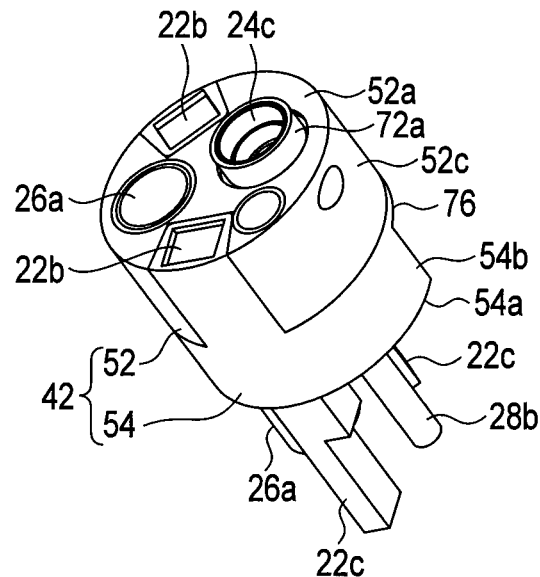
FIG. 10A is a schematic perspective view illustrating, from the distal-end side, a state in which small-sized light sources of the illumination optical systems, a lens frame of the observation optical system, the channel tube, and the AW tube have been attached to the distal-end rigid section of the endoscope according to the third embodiment.
Figure 10B:
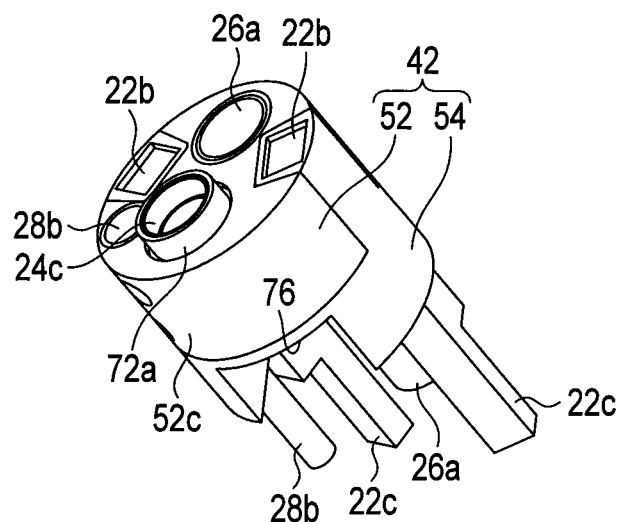
FIG. 10B is a schematic perspective view illustrating, from the distal-end side, the state in which the small-sized light sources of the illumination optical systems, the lens frame of the observation optical system, the channel tube, and the AW tube have been attached to the distal-end rigid section of the endoscope according to the third embodiment.

When the endoscope 10 is assembled (manufactured), as illustrated in FIG. 8A and FIG. 8B, the illumination windows 22a of the illumination optical systems 22, the observation window 24a of the observation optical system 24, the distal end of the channel tube 26b of the channel 26 and the distal end of the AW tube 28c of the air-feed/water-feed conduit 28 are opposed to the proximal-end side of the second base 54 of the distal-end rigid section 42. As described in the first embodiment, the illumination optical systems 22 and observation optical system 24 are disposed and fixed in the distal-end rigid section 42. As illustrated in FIG. 9A and FIG. 9B, the distal end of the channel tube 26b is connected and fixed to the proximal end of the channel pipe 26a, and the distal end of the AW tube 28c is connected and fixed to the proximal end of the AW pipe 28b. On the other hand, the nozzle 28a is connected and fixed to the distal end of the AW pipe 28b.

Thus, when the endoscope 10 is to be repaired by removing the distal-end rigid section 42 of the endoscope 10, it should suffice if the members, other than the channel pipe 26a and AW pipe 28b, are removed, with the channel pipe 26a and AW pipe 28b being left on the second base 54. Thus, there is no need to fix pipe-shaped members, such as the channel pipe 26a and AW pipe 28b, to the distal-end rigid section 42 by using an adhesive. Accordingly, it is possible to control the use of the adhesive, and to control the variance in quality at a time of reattaching the illumination optical systems 22 and observation optical system 24, and attaching the channel tube 26b, nozzle 28a, and AW tube 28c. Therefore, with the endoscope 10 according to this embodiment, the efficiency in manufacture and repair can be enhanced.

Even when the distal-end rigid section 42 is formed in the above manner, the same advantageous effects as described in connection with the first embodiment can be obtained.

Next, a third embodiment is described with reference to FIG. 10A to FIG. 10D. This embodiment is a modification of the first and second embodiments. The parts, which are identical to, or have the same functions as, the parts described in the first and second embodiments, are denoted by like reference numerals when possible, and a detailed description thereof is omitted.

This embodiment is an example in which, as illustrated in FIG. 10A to FIG. 10D, the AW pipe (pipe-shaped member) 28b and channel pipe (pipe-shaped member) 26a are formed integral with the distal-end rigid section 42 described in the first embodiment, and furthermore the lens frame (pipe-shaped member) 24c is integrally formed. Specifically, the second base 54 is formed on the first base 52, and the lens frame 24c, channel pipe 26a and AW pipe 28b are formed integral as one piece with the second base 54. Thus, there is no need to fix the lens frame 24c, channel pipe 26a, and AW pipe 28b to the second base 54 by using an adhesive, and the manufacturing cost and repair cost can be reduced at the time of manufacture and repair of the endoscope 10.

In addition, in this embodiment, the small-sized optical source boards 22c are further made integral with the distal-end rigid section 42 described in the first embodiment. Specifically, the second base 54 is formed on the first base 52, and the small-sized optical source boards 22c are further made integral with the second base 54. Thus, there is no need to fix the small-sized optical source boards 22c to the second base 54 by using an adhesive, and the manufacturing cost and repair cost can be reduced at the time of manufacture and repair of the endoscope 10.

When the illumination optical system 22 is formed, the small-sized light source 22b is attached to the distal end of the small-sized light source board 22c, and the lead wires 22d are attached to the proximal-end side of the small-sized light source board 22c.

When the observation optical system 24 is formed, the lenses 24d are disposed in the lens frame 24c from the distal-end side and proximal-end side of the distal-end rigid section 42, covering is provided by the observation window 24a, and the imaging unit 24e, which is integral with the imaging cable 24f, is fixed. It is also preferable that the imaging cable 24f be attachable/detachable to/from the imaging unit 24e.

Thus, when the endoscope 10 is to be repaired by removing the distal-end rigid section 42 of the endoscope 10, it should suffice if the members, other than the lens frame 24c, channel pipe 26a, and AW pipe 28b, are removed, with the lens frame 24c, channel pipe 26a, and AW pipe 28b being left on the second base 54. Therefore, there is no need to fix structural parts, such as the channel pipe 26a and AW pipe 28b, to the distal-end rigid section 42 by using an adhesive. Accordingly, it is possible to control the use of the adhesive, and to control the variance in quality at a time of reattaching the small-sized light source board 22c and lens frame 24c, and attaching the channel tube 26b, nozzle 28a, and AW tube 28c. Therefore, with the endoscope 10 according to this embodiment, the efficiency in manufacture and repair can be enhanced.

Even when the distal-end rigid section 42 is formed in the above manner, the same advantageous effects as described in connection with the first and second embodiments can be obtained.

As has been described above, according to these embodiments, the following can be said.

A distal-end rigid section of an insertion section of an endoscope includes a first base of a metallic material with a columnar shape, the first base including a circular through-hole penetrating in an axial direction of the insertion section and a non-circular through-hole which is juxtaposed with the circular through-hole and is accessible to an outer peripheral surface of the first base; and a second base of a resin material with an electrical insulation property, the second base being airtightly and watertightly formed as one piece with the first base on an axially proximal-end side of the first base, the second base airtightly and watertightly covering inner peripheral surfaces of the circular through-hole and the non-circular through-hole from the first base, a hole portion being formed on an inside of the covered inner peripheral surface of the non-circular through-hole such that at least one of an illumination light source and a light source board disposed on a proximal-end side of the illumination light source is disposed in the hole portion.

In the case of attaching the distal-end rigid section at a time of manufacturing the endoscope, or in the case of performing such repair as detaching the distal-end rigid section from the endoscope or re-attaching the distal-end rigid section, no part for securing insulation properties is needed at a time of attaching the observation optical system, illumination optical system, and nozzle to the distal-end rigid section. Thus, the number of parts can be reduced when various parts are attached, and the variance in quality at a time of attaching various parts can be controlled. In addition, since no part for ensuring insulation properties is needed, the use of an adhesive can be decreased. Thus, there is no need to provide a space for attaching the part, or such a space can be reduced even if the part is provided. Accordingly, the outside diameter of the insertion section can be reduced. Besides, the outer periphery of the illumination light source is surrounded by the second base of the resin material. It is thus possible to prevent the heat, which is produced from the illumination light source, from being radiated to the outside at a position near the distal-end rigid section.

Therefore, according to the above-described embodiments, there can be provided a distal-end rigid section of an insertion section of an endoscope, and an endoscope using this distal-end rigid section, the distal-end rigid section having high efficiency in manufacture and repair with little variance in quality when various parts are attached, being capable of reducing the diameter of the insertion section even when a small-sized illumination light source which can obtain a proper light amount is directly disposed, and being capable of preventing heat, which occurs from the small-sized illumination light source, from being directly radiated to the outside.

In addition, it is preferable that the hole portion of the second base be formed in a shape corresponding to the outer shape of the illumination light source.

When the illumination light source with a non-circular outer shape, such as an LED, is attached to the distal-end rigid section, since the shape corresponding to the outer shape of the illumination light source can be formed by the second base, work such as filling a resin material between the circular hole and the non-circular illumination light source is not needed. In addition, in general, since a circular hole requires an outside diameter which is equal to or greater than a maximum diagonal of a part that is to be attached, the outside diameter of the distal-end rigid section tends to become larger. However, in this invention, it should suffice if a hole smaller than the circular hole is formed. Thus, the diameter of the insertion section can be reduced. Furthermore, when heat is produced from the illumination light source, the outer periphery of the illumination light source is surrounded by the second base. It is thus possible to prevent the heat, which is produced from the illumination light source, from being radiated to the outside at a position near the distal-end rigid section.

Besides, it is preferable that the non-circular through-hole of the first base be formed in such a tapered shape as to be narrower on the side near the center axis of the first base than on the outer peripheral side of the first base.

Moreover, it is preferable that a pipe-shaped member be fixed in an electrically insulated state from the first base, at that position of the second base, which covers the inner peripheral surface of the circular through-hole of the first base.

Thus, there is no need to fix the pipe-shaped member to the distal-end rigid section by using an adhesive.

In addition, it is preferable that the illumination light source be fixed in an electrically insulated state from the first base, in the non-circular hole of the second base.

Thus, there is no need to fix the illumination light source to the distal-end rigid section by using an adhesive.

It is also preferable that the distal-end insulation layer, which covers the distal-end side of the first base, be airtightly and watertightly formed integral with the first base.

Thus, the electrical insulation of the first base of the metallic material can be positively ensured.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A distal-end rigid section of an insertion section of an endoscope, the distal-end rigid section comprising:
 a first base of a metallic material configured to form a distal-end portion of the insertion section of the endoscope;
 a second base of a resin material disposed on an axially proximal-end side of the first base;
 a first through-hole formed by opening a part along an outer peripheral surface of the first base;
 a cylindrical portion covering an inner peripheral surface of the first through-hole, hole, the cylindrical portion protruding from the second base toward an axially distal-end side of the first base and including a non-circular hole portion in which an illumination light source having a non-circular outer shape is disposed, the illumination light source generating light and emitting illumination light; and
 a circular-cylindrical portion formed by the second base and covering an inner peripheral surface of a second through-hole, is the circular-cylindrical portion being juxtaposed with the first through-hole and penetrating in an axial direction of the first base, wherein
 a pipe-shaped member is integrally fixed in the circular-cylindrical portion in a state in which the pipe-shaped member is electrically insulated from the first base, and the resin material of the second base is configured to prevent radiation of heat produced from the illumination light source toward an exterior of the distal-end rigid section.

2. The distal-end rigid section of claim 1, wherein the second base has an electrical insulation property.

3. The distal-end rigid section of claim 1, wherein the first through-hole is non-circular.

4. The distal-end rigid section of claim 3, wherein the second through-hole is circular.

5. The distal-end rigid section of claim 1, wherein the hole portion of the cylindrical portion is formed in a shape corresponding to an outer shape of at least one of the illumination light source and a light source board.

6. The distal-end rigid section of claim 1, wherein the first through-hole is formed at a position where a side near a center axis of the first base is closer to the first base than an outer peripheral side of the first base.

7. The distal-end rigid section of claim 1, wherein a distal-end insulation layer which covers a distal-end side of the first base is airtight, watertight and formed as one piece with the first base.

8. The distal-end rigid section of claim 1, wherein the cylindrical portion is formed such that a first circumferential thickness on the side of the first through-hole is greater than a radial thickness on a center axis side of the distal-end rigid section.

9. An endoscope comprising:
a first base of a metallic material forming a distal-end portion of an insertion section of the endoscope;
a second base of a resin material disposed on an axially proximal-end side of the first base;
a first through-hole formed by opening a part along an outer peripheral surface of the first base;
an illumination optical system including an illumination light source having a non-circular outer shape and emitting light when supplied with electrical power;
a cylindrical portion covering an inner peripheral surface of the first through-hole, hole, the cylindrical portion protruding from the second base toward the axially distal-end side of the first base and including a non-circular hole portion in which the illumination light source is disposed; and
a circular-cylindrical portion formed by the second base and covering an inner peripheral surface of a second through-hole, the circular-cylindrical portion being juxtaposed with the first through hole and penetrating in an axial direction of the first base, wherein
a pipe-shaped member is integrally fixed in the circular-cylindrical portion in a state in which the pipe-shaped member is electrically insulated from the first base, and
the resin material of the second base is configured to prevent radiation of heat produced from the illumination light source toward an exterior of the distal-end rigid section.

10. The endoscope of claim 9, wherein the illumination light source is a light-emitting diode (LED).

11. The endoscope of claim 9, wherein the hole portion of the cylindrical portion is formed in a shape corresponding to an outer shape of at least one of the illumination light source and a light source board.

12. The endoscope of claim 9, wherein the cylindrical portion is formed such that a first circumferential thickness on the side of the first through-hole is greater than a radial thickness on a center axis side of the distal-end rigid section.

* * * * *